United States Patent [19]

Hahn

[11] Patent Number: 4,613,121
[45] Date of Patent: Sep. 23, 1986

[54] X-RAY EXAMINATION TABLE

[75] Inventor: Alfred Hahn, Erlangen, Fed. Rep. of Germany

[73] Assignee: Siemens Aktiengesellschaft, Berlin & Munich, Fed. Rep. of Germany

[21] Appl. No.: 669,802

[22] Filed: Nov. 9, 1984

[30] Foreign Application Priority Data

Dec. 15, 1983 [DE] Fed. Rep. of Germany ....... 3345434

[51] Int. Cl.$^4$ ............................................. A61G 13/00
[52] U.S. Cl. ................................................. 269/322
[58] Field of Search .................. 187/18; 269/322, 323; 254/9 C, 122, 102; 182/63, 141, 148; 328/209

[56] References Cited

U.S. PATENT DOCUMENTS 2,096,022 10/1937 Akins .................................. 254/102
4,157,743 6/1979 Masuda et al. ........................ 187/18

Primary Examiner—Robert C. Watson
Attorney, Agent, or Firm—Hill, Van Santen, Steadman & Simpson

[57] ABSTRACT

An X-ray examination table having a height-adjustable trestle on which a patient support platform is mounted, characterized by the trestle having a liftable member on which the table is mounted being connected to a base by a double-jointed support arrangement and being movable to the base by a lifting arrangement. The double-jointed support arrangement includes a pair of brackets pivotally connected together and having one of the pair being pivotally connected to the liftable member and the other being pivotally connected to the base. The pivotal connections are shafts which extend parallel to each other for each linkage arrangement and perpendicular to the shafts of the adjacent linkage arrangement so that the double-jointed supports guide the liftable member as it is moved between the upper and lowermost positions.

3 Claims, 5 Drawing Figures

X-RAY EXAMINATION TABLE

BACKGROUND OF THE INVENTION

The present invention is directed to an x-ray examination table having a trestle on which a patient support platform is height-adjustably mounted.

X-ray examination tables in which a patient support platform is height-adjustably mounted on a trestle are utilized in angiography for the visualization or representation of blood vessels. A known examination table for this purpose is illustrated in FIG. 1 of the present application and has a patient support platform 1 which is mounted on a base or trestle 2 in a fixed relationship in two mutually perpendicular directions to form a horizontal plane. The trestle 2 is height-adjustable. The platform 1 is illustrated in heavy lines in a lower or low position and has a maximum vertical lift to the uppermost position which is illustrated in broken lines. The maximum height of this lift is d. The dimensions of the trestle are indicated by a and b with a height c.

For angiography, it is desirable that the dimensions a and b be as small as possible in order that the patient will be readily accessible to the physician from all sides. In addition, the dimension c is to be kept as small as possible so that the patient support platform 1 is capable of being lowered to the necessary position in order that a simple repositioning of the patient from a bed to the patient support platform is possible. Finally, the dimension d is to be as great as possible so that an optimum working height for the physician can be obtained.

In the case of known x-ray examination tables, the described optimum dimensions are only incompletely obtained or with a high cost, for example, in the case of a ceiling suspension.

SUMMARY OF THE INVENTION

The present invention is directed to providing an x-ray examination table on which a patient platform is mounted for adjustable movement on a trestle which examination table has a simple construction, a small area for the trestle, a low minimum table height and an optimum working height during examination procedures.

In order to obtain these objects, the present invention is directed to an improvement in an x-ray examination table having a height-adjustable trestle on which the patient support platform is mounted, the improvements being that the trestle includes a base and a liftable member, said platform being mounted on the liftable member, said trestle including height adjustment means for lifting the liftable member between a low position and a raised position relative to the base and guide means for guiding the liftable member as it is moved between said low and high positions. The guide means includes two first shafts mounted on the liftable member in a horizontal plane and extending perpendicular to each other, a separate linkage arrangement pivotally connected to each of the first shafts and including a first jacket arm secured to the first shaft for pivoting thereon, a second bracket pivotally connected to the first bracket by a second shaft extending parallel to the first shaft and said second bracket being pivotally connected to the base by a third shaft extending parallel to the first and second shafts. With this arrangement, each of the linkage arrangements forms a double-jointed support which connects in an articulate fashion about two horizontal shafts disposed perpendicular to one another and which exhibits two hinge brackets which are pivotable about two parallel horizontal shafts which are disposed parallel to the shaft of the pivot joint on the lifting member so that the rotating or swiveling shafts of the two double-jointed supports are disposed perpendicular to one another and that the height adjustment mechanism will engage the lifting member. The elements on which the two double-jointed supports consist, from the point of view of their dimensions, give a sufficient lift of the lifting member and can be kept small and therefor occupy little space in the trestle. The height adjustment mechanism can be arranged in a simple fashion beneath the lifting member where space is available.

In an expedient embodiment of the x-ray examination table according to the invention, the height adjustment mechanism is formed by a column disposed beneath the liftable member which is capable of traveling from a low position to an extended position by means of a motor. This column consists of several lifting spindles or screws which are provided with internal and external threads fitting into one another. The innermost lifting spindle can be rotated by a motor means. Given a low minimum overall height, an optimum lift is thereby possible.

DESCRIPTION OF THE PREFERRED EMBODIMENTS

Figure 3:
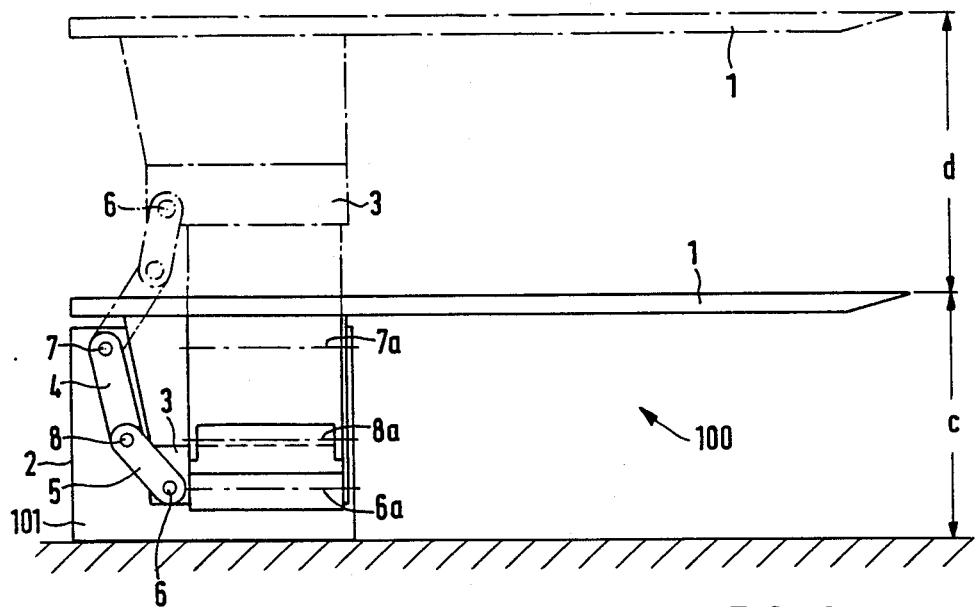
FIG. 3 is a side view of the x-ray examination table in accordance with the present view illustrated in the lowermost position and shown in the uppermost position in chain lines.

The principles of the present invention are particularly useful in an x-ray examination table generally indicated at 100 in FIG. 3. The x-ray examination table 100 has a patient support platform 1 which is mounted on a liftable member 3 which is illustrated as being received in a base 101 of a trestle 2.

Figure 1:
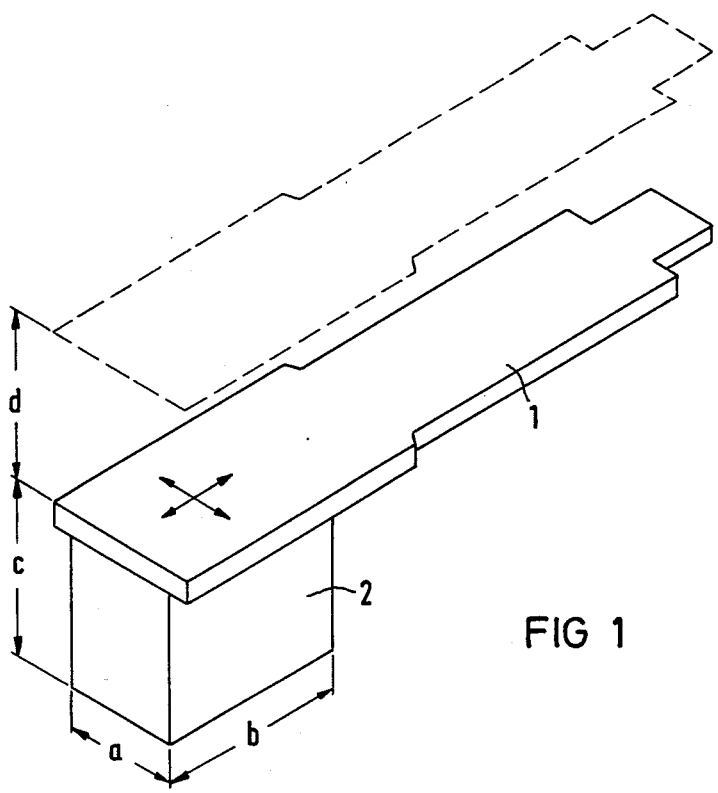
FIG. 1 as mentioned hereinabove is a perspective view of previously known x-ray examination tables.
Figure 2:
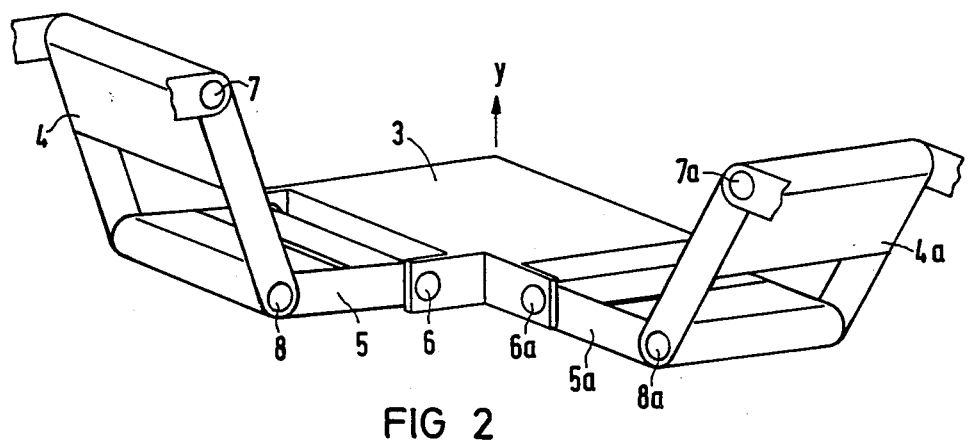
FIG. 2 is an perspective view illustrating the linkage arrangements connected to a portion of the lifting member.

As best illustrated in FIGS. 2 and 3, the guide means includes a pair of shafts 6 and 6a which lie in a horizontal plane and are connected to a portion of a lifting member such as 3 (see FIG. 2) and extend perpendicular to each other. Connected to each of these first shafts 6 and 6a is a linkage arrangement which includes a bracket 5 or 5a which is pivotally connected on the shaft 6 and is pivotally connected to a second bracket 4 or 4a, respectively, by a second shaft 8 or 8a which in turn extends parallel to the respective shafts 6 and 6a. The second bracket 4 at its end opposite the end connected to the shaft 8 has a third shaft 7 which connects it as best illustrated in FIG. 3 to a portion of the base 101 of the trestle 2. Each of the linkage arrangements which include the two brackets such as 4 and 5 with their respective shafts 7, 8 and 6 form a double-jointed support for connecting one side of the liftable member 3 to the base 101. As illustrated, the base 101 is a box-shaped member which telescopically receives the liftable member 3 which is illustrated as having a portion 3a that extends between the base portion that is connected to the linkage arrangement and the platform 1.

Figure 4:
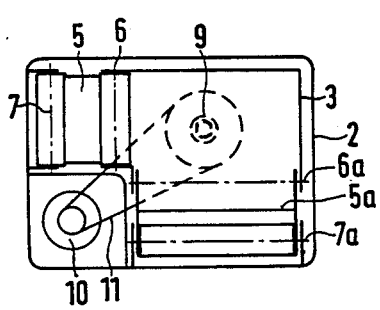
FIG. 4 shows a plan view of the trestle of the x-ray examination table according to FIG. 3.
Figure 5:
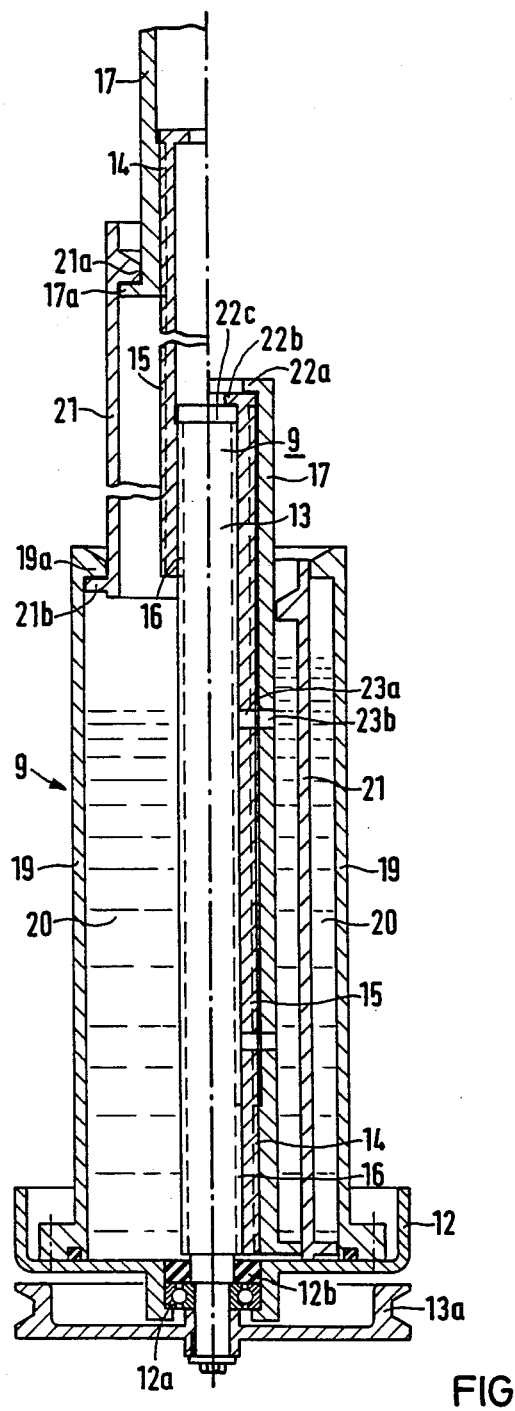
FIG. 5 is a longitudinal cross-sectional view taken of the lifting apparatus with the right-hand side showing it in the lowermost position and the upper portion showing the apparatus in an extended position.

In order to raise the platform 1 from the position illustrated in FIG. 3 in bold lines to the raised position illustrated in chain lines, a lifting means which is best illustrated in FIGS. 4 and 5 is provided. The lifting means or height adjustment mechanism comprises a column 9 which is driven by an electric motor 10 through a V belt 11. As illustrated, the electric motor can be disposed in the space between the double acting joint supports 4 and 5 and 4a and 5a.

As best illustrated in FIG. 5, the column 9 exhibits a first lifting spindle 13 which is rotatably mounted in a base member 12 by a bearing 12a. A seal 12b seals the space above the base member 12 in an oil-tight fashion. The lifting spindle 13 is rotated by a pulley 13a which receives the V belt 11. The lifting spindle 13 has external threads which are in threaded engagement with internal threads 16 of a second lifting spindle 15. The second lifting spindle 15 has external threads 14 which in turn are in threaded engagement with internal threads of a tube 17 whose upper end 22a is connected to the liftable member such as 3.

Lubrication is guaranteed by a lubricating oil 20, which is contained in an oil receptacle 19 which is sealingly received in a receptacle 12. An oil spray collector 21 will return the oil being thrown off of the lifting spindle such as 15 in case of a full lift and return the oil to the receptacle 19. As illustrated, the collector 21 at its upper end has an internal shoulder 21a which is engaged on an external shoulder 17a on the lower end of the tube 17. In a similar manner, the receptacle 19 has an inner shoulder 19a on its upper end which engages a lower external shoulder 21b on the collector 21 to prevent its passage beyond a maximum height.

As illustrated in FIG. 5 on the right-hand side of the drawing, the spindles are in their lowermost position. If the table 1 is to be raised, then the motor is actuated to rotate the pulley 13a to rotate the spindle 13 to cause lifting of the spindle 15 and the tube 17 upwardly toward the position illustrated in the left-hand side of the Figure. In the case of movement of the tube 17 upwardly, it is noted that the oil spray collector 21 will be engaged as the tube raises above a certain height to carry it upward with the tube 17. The lower stops such as 22a, 22b and 22c serve the purpose of limiting the movement of the sleeves and tubes relative to each other. Bores such as 23a and 23b are provided in the spindle 15 and tube 17 to insure that the threads are always in contact with oil.

Returning to FIG. 3, it is noted that when the platform 1 is in its lowermost position at a height c above the floor, the brackets 4 and 5 for the linkage arrangement are such that the shaft 7 connected to the base is substantially higher than the shaft 6 which is connected to the liftable member 3. Once the drive mechanism or lifting mechanism is actuated, the various brackets 4 and 5 and 4a and 5a will pivot to allow the liftable member 3 to be moved upwardly toward the position illustrated in chain line wherein the shaft 6 will be above the shaft 7. It should be noted that while the linkage arrangements on one side will allow movement in a direction perpendicular to the axis of the shaft 7, the second arrangement which extends perpendicularly thereto prevents movement in that direction so that the liftable member 3 is guided while being moved in the vertical direction.

Although various minor modifications may be suggested by those versed in the art, it should be understood that I wish to embody within the scope of the patent granted hereon, all such modifications as reasonably and properly come within the scope of my contribution to the art.

I claim:

1. In an x-ray examination table comprising a trestle on which a patient support platform is mounted for height adjustability, the improvements comprising the trestle including a base and a liftable member, said platform being mounted on the liftable member, said trestle including height adjustment means for lifting the liftable member between a lowermost position and a raised uppermost position relative to the base and guide means for guiding the liftable member as it is moved between said positions, said guide means including two first shafts mounted on the liftable member in a horizontal plane and extending perpendicularly to each other, a separate linkage arrangement pivotally connected to each of said first shafts and including a first bracket arm secured to the first shaft for pivoting thereon, a second bracket arm pivotally connected to the first bracket arm by a second shaft extending parallel to the first shaft and said second bracket arm being pivotally connected to the base by a third shaft extending parallel to the first and second shafts, said base including an open box-like member telescopically receiving the liftable member when the liftable member is in the lowermost position, said first shafts of the liftable member being substantially below the level of the second and third shafts when the liftable member and table are in the lowermost position and with the liftable member in the uppermost position, the liftable member being raised completely out of the base with the first shafts being disposed above the second and third shafts of each of the linkage arrangements.

2. In an x-ray examination table according to claim 1, wherein the height-adjustment means is formed by a column capable of being extended by a motor means, said column being positioned beneath the liftable member.

3. In an x-ray examination table according to claim 2, wherein the column consists of several lifting spindles telescopically received in one another and provided with interengaging internal and external threads, and the innermost lifting spindle being rotated by said motor means.

* * * * *